United States Patent [19]

Kaiser

[11] 3,974,102
[45] Aug. 10, 1976

[54] MIXED METAL CATALYST FOR ISOMERIZATION OF ALPHA-PINENE TO BETA-PINENE

[75] Inventor: Gregory L. Kaiser, West Jacksonville, Fla.

[73] Assignee: SCM Corporation, New York, N.Y.

[22] Filed: May 12, 1975

[21] Appl. No.: 576,744

[52] U.S. Cl. .................... 252/466 J; 252/466 PT; 260/675.5
[51] Int. Cl.² .................... B01J 21/04; B01J 23/58; B01J 23/72; B01J 23/78
[58] Field of Search ................ 252/466 PT, 466 J; 260/675.5

[56] References Cited
UNITED STATES PATENTS 3,679,746   7/1972   Brake ........................... 252/466 PT
3,789,020   1/1974   Carter et al. .................. 252/466 PT

*Primary Examiner*—W. J. Shine
*Attorney, Agent, or Firm*—Jerry K. Mueller, Jr.

[57] ABSTRACT

A Group VIII catalyst admixed with a Group IB metal (mixed metal catalyst) for the isomerization of alpha-pinene to beta-pinene is disclosed. The mixed metal catalyst preferably is disposed on an alumina support and the acidic functionality displayed by said supported mixed metal catalyst is neutralized in a neutralization treatment with an alkali metal or alkaline earth metal salt or hydroxide.

9 Claims, No Drawings

MIXED METAL CATALYST FOR ISOMERIZATION OF ALPHA-PINENE TO BETA-PINENE

This invention relates to a Group VIII catalyst for the catalyzed isomerization of alpha-pinene to beta-pinene and more particularly to admixing a Group IB metal with the Group VIII catalyst to increase the activity and specificity of the catalyst for beta-pinene formation.

BACKGROUND OF THE INVENTION

This application is cross-referenced to the commonly assigned application U.S. Ser. No. 576,718 of Gregory Kaiser, filed on even date herewith, entitled "Catalyst for Isomerization of Alpha-Pinene to Beta-Pinene", the disclosure of which is expressly incorporated herein by reference.

The catalyzed isomerization of alpha-pinene to beta-pinene to which this invention is disclosed in U.S. Pat. No. 3,278,623, the disclosure of which is expressly incorporated herein by reference. The isomerization is carried out in the presence of a transitory hydrogen acceptor catalyst using hydrogen gas as a co-catalyst. A preferred hydrogen acceptor catalyst is a Group VIII metal on an aluminum support.

Such isomerization process also produces acidic by-products, hydrogenation products, and polymerization products of the initial alpha-pinene feed supply. These related byproducts decrease the selectivity of the Group VIII catalyst for beta-pinene formation. Kaiser in U.S. Ser. No. 576,718 discloses a method for substantially suppressing the acidic byproduct formation by subjecting the alumina-supported Group VIII catalyst to a neutralization treatment in order to neutralize the acid functionality displayed by the catalyst.

Heretofore, Inami et al. reported that contacting 1-butene with a gold catalyst caused isomerization to 2-butene, and contacting 1-butene with a palladium catalyst caused dehydrogenation. (Isomerization and Dehydrogenation of Butene Catalyzed by Nobel Metals and Their Alloys, Journal of Catalysis, Vol. 13, pp. 397–403 (1969)). These authors further reported that up to 40 atom-percent palladium can be alloyed with the gold without undue loss of isomerization activity of 1-butene to 2-butene.

In "Olefin Hydrogenation Catalyzed by Supported and Unsupported Mixed Metals," Journal of Catalysis, Vol. 26, pp. 92–96 (1972), Inami et al. reported that a palladium-gold unsupported catalyst is useful in catalytically hydrogenating cyclopentene and that an alumina-supported palladium-gold (up to 25 atom-percent gold) catalyst is useful in catalytically hydrogenating benzene.

It is an object of the present invention to increase the percent conversion (specificity) of Group VIII catalyst for the formation of beta-pinene and at the same time retain high selectivity of the catalyst for beta-pinene formation.

For purposes of this application, selectivity is measured as a function of all byproducts formed during the isomerization process, and is calculated as follows:

$$\text{SELECTIVITY} = \frac{\% \text{ beta-pinene formed}}{\% \text{ alpha-pinene totally converted}} \times 100\%$$

By suppressing by-product formation, selectivity is increased. Specificity is measured as a function of the degree of conversion of alpha-pinene to beta-pinene during the isomerization process and is calculated as follows:

$$\text{SPECIFICITY} = \frac{\text{beta-pinene formed (weight)}}{\text{initial alpha-pinene feed supply (weight)}} \times 100\%$$

DESCRIPTION OF THE INVENTION

The present invention resides in the discovery that the specificity of a Group VIII catalyst for the formation of beta-pinene can be increased while still retaining a very high selectivity of the catalyst by admixing a Group IB metal with the Group VIII catalyst (mixed metal catalyst).

Also disclosed herein is an improved alumina-supported Group VIII catalyst admixed with a Group IB metal which displays substantially no acidic functionality, even in the presence of hydrogen, such catalyst being especially useful in the catalyzed isomerization of alpha-pinene to beta-pinene wherein neutral to basic conditions must be maintained in order to suppress acidic by-product formation during such isomerization.

The Group IB metals useful in the present invention include copper, gold, and silver; silver being the preferred Group IB metal. At least 1 atom-percent of the Group IB metal should be admixed with the catalyst according to the precepts of the present invention. The Group IB metal can range up to 99 atom-percent, but with such high content of the Group IB metal (and low Group VII catalyst amount) there is generally insufficient Group VIII catalyst for economic and efficient operation of the isomerization process. Advantageously, the Group IB metal is present in an amount of about 1–50 atom-percent, and preferably between about 1 and 10 atom-percent.

At Group IB metal amounts of about 40–50 atom-percent optimum selectivity and specificity are obtained, but activity of the catalyst becomes reduced after a period, for instance, about 4–6 months. At lower Group IB amounts of about 1–10 atom-percent, long-term activity of the catalyst is obtained as well as significant increases in selectivity and specificity for beta-pinene formation (as compared to the catalyst sans any Group IB metal).

The atom-percent of the Group IB as Group VIII metal is calculated by dividing the atomic weight of the metal by actual weight present. Thus, 40 atom-percent of gold (atomic weight—196.9) and 60 atom-percent palladium (atomic weight—106.4) corresponds to 78.79 grams of gold and 63.84 grams of palladium.

The catalyst is admixed with a Group IB metal (mixed metal catalyst). For purposes of this application, the catalyst admixed with a Group IB metal includes an alloy thereof, mixed metal powders thereof, and the mixed metals disposed on an inert support. In order to obtain the maximum surface area of both the catalyst and Group IB metal for maximum isomerization of the alpha-pinene supply, the catalyst and Group IB metal preferably and advantageously are disposed on an inert support, such as alumina.

Applicant theorizes that the Group IB metals provide desorption sites for the beta-pinene formed during the isomerization process. If the beta-pinene molecule remains in contact with the catalyst too long, hydrogenation and skeletal rearrangement of the beta-pinene molecule can occur. The Group IB metal, thus effectively causes the isomerized beta-pinene molecules to desorb at a higher rate (less catalyst contact time) than if no Group IB metal was present with the catalyst.

The alpha-pinene isomerization process is acutely acid sensitive as acidic conditions in the process can deactivate an otherwise active Group VIII catalyst and will cause formation of undesirable acidic by-products (such as camphene, cymene, and limonene). Formation of acid by-products during the alpha-pinene isomerization process decreases the selectivity of the alumina-supported Group VIII catalyst for beta-pinene formation.

Commercially prepared Group VIII catalysts admixed with a Group IB metal on an alumina support can have residual anions thereon, which anions can form acid in the presence of hydrogen. Such commercial preparation generally comprises treating alumina with an aqueous salt solution of the Group VIII catalyst and Group IB metal followed by drying and subsequent reduction in a basic hydrazine solution or in flowing hydrogen gas. Residual anions remain on the alumina-supported catalyst even after the reduction step. These residual anions can form acid when contacted with co-catalyst hydrogen gas during the isomerization process which can cause the aforementioned acidic by-product formation. Group VIII catalyst and Group IB metal salts used in the commercial preparation of the subject catalysts can include the salts of chlorine, bromine, iodine, fluorine, nitrate, sulfate, and the like.

Most forms of alumina readily hydrate to form acid sites (hydroxyl groups) whereon which hydroxyl groups can serve as a source of protons, the alumina displaying acidic functionalities thereby. The residual anions further can exchange with such hydroxyl groups which exchange intensifies the electronegativity of the acid sites. Such acid sites on the alumina support also can cause the aforementioned acidic by-product formation.

The acidic functionality displayed by the Group VIII catalyst admixed with Group IB metal on an alumina support can be suppressed by subjecting the supported catalyst and Group IB metal to a neutralization treatment. This involves treating the supported catalyst and Group IB metal with at least about 0.002 weight parts per weight part of alumina of an alkali metal or alkaline earth metal neutralizing agent provided from an alkali metal or alkaline earth metal salt or hydroxide inert to the catalyst. For purposes of this application the term "alkali metal" includes sodium, lithium, potassium, rubidium, and cesium; and the term "alkaline earth metal" includes calcium, strontium, barium, and magnesium.

Treatment with about 0.002 weight parts of the neutralizing agent generally is sufficient to affect a significant neutralization of the acidic functionality displayed by the supported catalyst and Group IB metal and concomitant suppression of most of the acid by-product formation during the alpha-pinene isomerization process, substantially complete neutralization being achieved with about 0.015 weight parts. Above about 0.015 weight parts, waste of the neutralizing agent can occur, though activity and selectivity of the catalyst normally will not be adversely affected by treatment with excess agent.

The alkali metal or alkaline earth metal salt or hydroxide preferably is dispersed in a solvent for treating the supported catalyst and Group IB metal. Water is a preferred solvent and, thus, some water solubility of the neutralizing agent is desirable. If the particular neutralizing agent is only slightly soluble in water, successive treatments of the alumina-supported catalyst and Group IB metal may be necessary. Such successive treatments are not injurious to the catalyst and Group IB metal, and in some instances are desirable to attain complete neutralization. The amount of water should be sufficient to satisfy the pore volume of the alumina.

Suitable neutralizing agents are alkali metal or alkaline earth metal carbonates, bicarbonates, hydroxides, nitrates, nitrites, acetates, formates, and oxylates as well as others that will be obvious to those skilled in the art particularly from the teachings of this application.

Following the neutralization treatment, the supported catalyst and Group IB metal are heated at a temperature of less than about the minimum sintering temperature of the catalyst. For purposes of this application, the "minimum sintering temperature" is that temperature above which the crystalline size of the catalyst will be altered and such catalyst rendered unsuitable for use in the isomerization of alpha-pinene.

The reason for this heating is that the anions of the neutralizing agent salts or hydroxides if left on the catalyst can combine with co-catalyst hydrogen during the alpha-pinene isomerization process to form acids or water, which acids or water are either deleterious to the isomerization process or to the separation of products following isomerization.

Preferably, the heating is carried out in the presence of added hydrogen to insure the total formation of compounds which are readily fugitive or decomposable at elevated temperatures.

For instance, neutralization treatment with sodium carbonate causes formation of carbonic acid, which readily decomposes to carbon dioxide and water under moderate heating of about 100°C. Applicant theorizes that when other neutralizing agents, such as sodium acetate, are employed in the treatment, that a corresponding anion, such as an acetate anion, is formed. Heating the treated supported catalyst and Group IB metal at about 120°C. and 1 atmosphere total pressure in the presence of hydrogen then causes the corresponding acid, such as acetic acid, to be formed and such acid readily evaporates at this temperature to yield a supported catalyst and Group IB metal free of the acetate anion.

As a general rule, the heating temperature need not exceed 180°C. Although the addition of hydrogen gas is preferred in order to insure that substantially all of the anions are combined with hydrogen to form the corresponding compound which can be evaporated or decomposed under heating, the hydrogen can be in-situ hydrogen from the hydroxyl group on the alumina support (acid site).

The in-situ hydrogen is believed to result from reaction of the alkali metal or alkaline earth metal neutralizing agent with the hydroxyl sites on the alumina. The neutralizing agent probably forms a corresponding oxide of the alkali metal or alkaline earth metal releasing disassociated hydrogen which is free to combine with the anion of the agent salt or hydroxide. It is understood of course that the alkali metal or alkaline earth metal salts which are formed in the neutralization treatment need not be removed from the supported catalyst prior to the isomerization process as such salts are not chemically deleterious to the isomerization process.

A theory explaining the formation of atomic hydrogen on alumina has been proposed by Kenneth M. Sancher in "Hydrogen Migration of Alumina/Palladium Catalysts for Benzene Hydrogenation," *Journal of Catalysis*, Vol. 20 pages 106–109 (1971), the same being incorporated herein by reference. Such proposal is that hydrogen atoms can come from chemisorbed hydrogen on the catalyst, which hydrogen migrates to the alumina support. Applicant theorizes that such migrated hydrogen combines with the hydroxyl groups to form an acid site (Broensted acid site) on the alumina support. The neutralization treatment of the present invention neutralizes at least a portion of these acid sites.

The preferred catalysts suitable for the alpha-pinene isomerization process, supported on an alumina support, are those elemental metals disclosed in U.S. Pat. No. 3,278,623, which are the Group VIII metals having an atomic number between 28 and 78, inclusive, (nickel, ruthenium, rhodium, palladium, osmium, iridium, and platinum). The preferred catalyst is elemental palladium and in this application the catalyst will be described with reference to palladium, although it will be apparent to those skilled in the art that other catalysts may be employed.

Alumina appears in various crystalline structures, such as alpha-alumina, theta-alumina, delta-alumina, gamma-alumina, etc., as more fully described in Kirk-Othmer Encyclopedia of Chemical Technology, Vol. 2, 2nd Edition, the same being incorporated herein by reference. The particular crystalline structure of the alumina for the alpha-pinene isomerization process is not critical. Various combinations of the different crystalline forms of the alumina also are beneficial.

The preferred aluminas are gamma-alumina and alpha-alumina, the former when used for the catalyst support providing the highest conversion to beta-pinene compared to other forms of alumina. Alpha-alumina on the other hand is the most effective form of alumina in suppressing formation of acid by-products. Thus, the greatest selectivity for beta-pinene formation is obtained by using alpha-alumina as the support for the catalyst. Alpha-alumina is chemically the most stable form of alumina and is resistant to forming hydroxyl acid sites thereon.

The isomerization reaction is carried out in a suitable vessel having means for supporting the catalyst and Group IB metal (supported or unsupported), by passing a stream of alpha-pinene in vapor or liquid form over the neutralized catalyst. A preferred carrier for the alpha-pinene stream is helium, with which is mixed about 2.0–8.0% hydrogen, as a co-catalyst, based on the moles of alpha-pinene being subjected to isomerization. Details of the catalyzed isomerization of alpha-pinene can be as practiced in U.S. Pat. No. 3,278,623.

The initial alpha-pinene supply may contain contaminants, such as sulfur, which poisons the catalyst during isomerization. Thus, it may be desirable to remove such contaminants in the alpha-pinene supply by pretreating such supply in accordance with the teachings of U.S. Pat. Nos. 3,325,553; 3,360,581; and 3,420,910, the same being incorporated herein by reference.

The following examples show in detail how the invention has been practiced, but should not be construed as limiting. In this specification, all parts are parts by weight, all percentages are weight percentages, and all temperatures are in degrees centigrade unless otherwise expressly indicated.

EXAMPLES

In all examples of this application, alpha-pinene was isomerized to beta-pinene according to the teachings of U.S. Pat. No. 3,278,623 under the following conditions.

| | |
|---|---|
| Reactor: | ⅜" I.D. by 5" pyrex tube with medium glass frit to support the catalyst |
| Catalyst: | Palladium |
| Group IB metal: | Silver or Gold |
| Support: | alpha-alumina (⅛" tablets) |
| Co-catalyst | Hydrogen gas, % $H_2$ expressed as molar ratio of $H_2$/alpha-pinene, varied between 0 and 7.5% |
| Reaction temperature: | 150°C. |
| alpha-pinene supply: | Liquid, admitted to reactor at 2.8–3.3 Torr (mm Hg) effectively sulfur-free supply |
| Carrier: | Helium gas |
| Contact time over catalyst: | 0.38 seconds or 0.13 seconds |
| Selectivity for beta-pinene: | $\dfrac{\% \text{ beta-pinene formed}}{\% \text{ alpha-pinene totally converted}} \times 100\%$ |
| Specificity for beta-pinene: | $\dfrac{\text{beta-pinene formed (wt.)}}{\text{initial alpha-pinene feed supply (wt.)}} \times 100\%$ |

The total weight of palladium and Group IB metal (silver or gold) was 2.0 grams. 0.5% by weight of the alumina support, of the palladium and silver or gold were disposed on the alumina support at different ratios of palladium to gold or silver. The general reaction procedure for disposing the palladium and gold or silver on the alumina support is as follows:

1. $Na_2PdCl_4$ and $HAuCl_4 \cdot 3H_2O$ each are weighed to determine the weight of palladium and gold needed to give the desired proportions of each metal;
2. the weighed amounts of $Na_2PdCl_4$ and $HAuCl_4 \cdot 3H_2O$ are added to sufficient water to satisfy the pore volume of the alpha-alumina (0.35 grams water per 1 gram alpha-alumina) and dissolved therein;
3. the alpha-alumina is added to the salt solution of step (2) and then dried over a steam bath while being agitated;
4. the salt-treated alumina support then is reduced by adding a basic hydrazine solution ($N_2H_4$ in a 0.5 N sodium hydroxide solution) under agitation for 30 minutes; and
5. the Pd-Au alumina supported catalyst is removed from the hydrazine solution, washed with water, and dried.

All of the supported catalysts and gold or silver were prepared in a manner similar to that above described method followed by further reduction in hydrogen gas at 350°C. for 2 hours. The supported catalysts and gold or silver were subjected to a neutralization treatment by adding $Na_2CO_3$ in aqueous solution thereto, followed by heating at 100°–150°C. for 1 hour. The amount of $Na_2CO_3$ used in the neutralization treatment varied for the different palladium-gold or silver supported catalysts as can be seen from the following examples.

EXAMPLE 1

Alumina-supported palladium catalysts admixed with varying amounts of gold were prepared as above-described and employed as the catalyst for the catalyzed isomerization of alpha-pinene to beta-pinene. A control sample (palladium catalyst without any gold) also was used. Further, the co-catalyst hydrogen gas amount was used at three different levels for each Pd/Au catalyst tested. The neutralization treatment employed 0.006 grams of sodium (from the $Na_2CO_3$) per gram of alumina. The contact time of the alpha-pinene supply with the catalysts was 0.38 seconds.

Complete details of the parameters of the isomerization process and results obtained are displayed in Table 1.

EXAMPLE 2

Alumina-supported palladium catalysts admixed with varying amounts of silver were employed for the catalyzed isomerization of the alpha-pinene to beta-pinene. The total metal (Pd plus Ag) loading on the alumina was 0.5 weight percent (based on the weight of the alumina). The Pd/Ag supported catalysts had been subjected to a neutralization treatment of 0.006 grams of sodium (from $Na_2CO_3$) per gram of alumina. The contact time of the alpha-pinene supply with the catalysts was 0.13 seconds. The amount of co-catalyst hydrogen was used at three different levels for each Pd/Ag catalyst tested.

Details and results of the various runs are given in Table 2.

TABLE 2

| Pd/Ag Atom Ratio | Product Distribution (vol%) | | | | | Total Conv. (%) | β-pinene | |
|---|---|---|---|---|---|---|---|---|
| | Consumed α-pinene | β-pinene | Pinane | Others | Total Hydrogenated Byproducts | | Selectivity (%) | Specificity (%) |
| 3.7% $H_2$ | | | | | | | | |
| 100/0 | 1.69 | 1.69 | .001 | tr | .010+ | 1.70 | 99.9 | 1.69 |
| 90/10 | 1.93 | 1.91 | .011 | .007 | .018 | 1.94 | 99.1 | 1.91 |
| 80/20 | 2.41 | 2.40 | .008 | .003 | .011 | 2.42 | 99.5 | 2.41 |
| 60/40 | 2.26 | 2.25 | .010 | .003 | .013 | 2.27 | 99.4 | 2.25 |
| 5.6% $H_2$ | | | | | | | | |
| 100/0 | 2.03 | 2.02 | .005 | .006 | .011 | 2.04 | 99.5 | 2.03 |
| 90/10 | 2.02 | 1.98 | .027 | .014 | .041 | 2.03 | 98.0 | 1.99 |
| 80/20 | 2.75 | 2.69 | .045 | .015 | .060 | 2.77 | 97.8 | 2.71 |
| 60/40 | 2.42 | 2.40 | .017 | .004 | .021 | 2.43 | 99.1 | 2.41 |
| 7.5% $H_2$ | | | | | | | | |
| 100/0 | 2.39 | 2.36 | .019 | .010 | .029 | 2.40 | 98.8 | 2.37 |
| 90/10 | 2.12 | 2.07 | .033 | .017 | .050 | 2.13 | 97.6 | 2.07 |
| 80/20 | 2.79 | 2.70 | .072 | .016 | .088 | 2.80 | 96.9 | 2.71 |
| 60/40 | 2.55 | 2.51 | .031 | .005 | .036 | 2.56 | 98.6 | 2.52 |

The above results demonstrate that the specificity for beta-pinene formation increased by the addition of silver to the palladium catalyst, while the high selectivity was substantially retained.

I claim:

1. A process for neutralizing the acidic functionality displayed by an alumina-supported Group VIII catalyst admixed with Group IB metal, wherein said Group VIII

TABLE 1

| Catalyst | | | Product Distribution (vol%) | | | | Total Conv. (%) | β-pinene | |
|---|---|---|---|---|---|---|---|---|---|
| Metal Loading Pd+Au (wt%) | Pd/Au Atom Ratio | Consumed α-pinene | β-pinene | Pinane | Others | Total Hydrogenated Byproducts | | Selectivity (%) | Specificity (%) |
| 3.7% $H_2$ | | | | | | | | | |
| 0.5 | 100/0 | 2.51 | 2.50 | .004 | .006 | .010 | 2.52 | 99.6 | 2.51 |
| 0.5 | 90/10 | 2.83 | 2.80 | .013 | .021 | .034 | 2.85 | 98.8 | 2.81 |
| 0.5 | 80/20 | 2.80 | 2.76 | .013 | .028 | .041 | 2.81 | 98.5 | 2.77 |
| 0.5 | 60/40 | 3.28 | 3.16 | .059 | .063 | .122 | 3.30 | 96.3 | 3.18 |
| 5.6% $H_2$ | | | | | | | | | |
| 0.5 | 100/0 | 3.21 | 3.00 | .129 | .079 | .208 | 3.22 | 93.5 | 3.01 |
| 0.5 | 90/10 | 3.31 | 3.00 | .149 | .063 | .212 | 3.23 | 93.4 | 3.01 |
| 0.5 | 80/20 | 3.42 | 3.13 | .222 | .067 | .289 | 3.43 | 91.6 | 3.14 |
| 0.5 | 60/40 | 3.53 | 3.17 | .255 | .109 | .364 | 3.55 | 89.7 | 3.18 |
| 7.5% $H_2$ | | | | | | | | | |
| 0.5 | 100/0 | 3.16 | 2.98 | .126 | .055 | .181 | 3.18 | 94.3 | 2.99 |
| 0.5 | 90/10 | 3.33 | 3.03 | .215 | .083 | .298 | 3.34 | 91.1 | 3.04 |
| 0.5 | 80/20 | 3.48 | 3.17 | .242 | .071 | .313 | 3.50 | 91.0 | 3.18 |

The above results demonstrate that the specificity of the palladium catalyst is increased by the addition of the gold thereto, while maintaining substantially the same high selectivity for beta-pinene formation.

catalyst and said Group IB metal are disposed on said alumina support by contacting said alumina support with a Group VIII and Group IB salt solution followed by drying and reduction, said reduced alumina-supported Group VIII catalyst and Group IB metal having residual anions remaining thereon, said Group VIII catalyst being an elemental Group VIII metal having an atomic number between 28 and 78, inclusive, and said anions forming acid when contacted by hydrogen, which comprises:
  a. treating said alumina-supported catalyst and Group IB metal with at least about 0.002 weight parts per weight part of said alumina support of an alkali metal or alkaline earth metal provided from a salt or hydroxide of an alkali metal or alkaline earth metal salt or hydroxide inert to said catalyst, said treatment resulting in the formation of a salt of an alkali metal or alkaline earth metal with said residual anions; and
  b. heating said treated alumina-supported catalyst and Group IB metal in the presence of hydrogen at a temperature less than about the minimum sintering temperature of said catalyst, the temperature of said heating being sufficient to volatilize or decompose the compound formed by the anion of said salt or hydroxide and said hydrogen.

2. The process of claim 1 wherein said elemental Group VIII metal is palladium.

3. The process of claim 1 wherein said Group IB metal is selected from the group consisting of silver and gold.

4. The process of claim 1 wherein said alumina is alpha alumina.

5. The process of claim 1 wherein said alumina is of the type having acid sites and at least a portion of said acid sites are neutralized by said treatment.

6. An alumina-supported Group VIII catalyst admixed with Group IB metal wherein said Group VIII catalyst and said Group IB metal are disposed on said alumina support by contacting said alumina support with a Group VIII and Group IB salt solution followed by drying and reduction, said reduced alumina-supported Group VIII catalyst and Group IB metal having residual anions remaining thereon, said Group VIII catalyst being an elemental Group VIII metal having an atomic number between 28 and 78, inclusive, the improvement wherein said alumina-supported catalyst and Group IB metal is neutralized following said reduction by treatment with at least about 0.002 weight parts per weight part of alumina support of an alkali metal or alkaline earth metal provided from a salt or hydroxide of alkali metal or alkaline earth metal said treatment resulting in the formation of a salt of an alkali metal or alkaline earth metal with said residual anions, followed by heating in the presence of hydrogen at a temperature less than about the minimum sintering temperature of said Group VIII catalyst, but at a temperature sufficient to volatilize or decompose the compound formed by the anion of said salt or hydroxide with said hydrogen.

7. The alumina-supported Group VIII catalyst and Group IB metal of claim 6, wherein said elemental Group VIII metal is palladium and said Group IB metal is selected from the group consisting of silver and gold.

8. The alumina-supported Group VIII catalyst and Group IB metal of claim 6 wherein said alumina support has acid sites thereon and at least a portion of said acid sites are neutralized by said treatment.

9. The alumina-supported Group VIII catalyst and Group IB metal of claim 8 wherein said elemental Group VIII catalyst is palladium and said Group IB metal is selected from the group consisting of gold and silver.

* * * * *